United States Patent
Meyer et al.

(10) Patent No.: US 12,019,008 B2
(45) Date of Patent: *Jun. 25, 2024

(54) MORPHOMETRIC DETECTION OF MALIGNANCY ASSOCIATED CHANGE

(71) Applicant: VISIONGATE, INC., Woodinville, WA (US)

(72) Inventors: Michael G. Meyer, Phoenix, AZ (US); Laimonas Kelbauskas, Chandler, AZ (US); Rahul Katdare, Bothell, WA (US); Daniel J. Sussman, Auburn, CA (US); Timothy Bell, Phoenix, AZ (US); Alan C. Nelson, Gig Harbor, WA (US)

(73) Assignee: VISIONGATE, INC., Woodinville, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/064,759

(22) Filed: Dec. 12, 2022

(65) Prior Publication Data

US 2023/0289407 A1  Sep. 14, 2023

Related U.S. Application Data

(63) Continuation of application No. 16/976,015, filed as application No. PCT/US2019/020093 on Feb. 28, 2019, now Pat. No. 11,551,043.

(Continued)

(51) Int. Cl.
*G01N 15/1433* (2024.01)
*G01N 15/14* (2006.01)
(Continued)

(52) U.S. Cl.
CPC ....... *G01N 15/1433* (2024.01); *G01N 15/147* (2013.01); *G01N 33/4833* (2013.01);
(Continued)

(58) Field of Classification Search
CPC .......... G06F 18/2148; G06F 18/24317; G01N 15/147; G01N 15/1475; G01N 33/4833;
(Continued)

(56) References Cited

U.S. PATENT DOCUMENTS

| 6,026,174 A | 2/2000 | Palcic et al. |
| 6,522,775 B2 | 2/2003 | Nelson |

(Continued)

FOREIGN PATENT DOCUMENTS

WO    2019/067557 A1    4/2019

OTHER PUBLICATIONS

Böcking et al., "Diagnosis of Bronchial Carcinoma on Sections of Paraffin-Embedded Sputum," *Acta Cytologica* 36(1):37-47, 1992.
(Continued)

*Primary Examiner* — Nay A Maung
*Assistant Examiner* — Jose M Torres
(74) *Attorney, Agent, or Firm* — Seed IP Law Group LLP

(57) ABSTRACT

A method for a system and method for morphometric detection of malignancy associated change (MAC) is disclosed including the acts of obtaining a sample; imaging cells to produce 3D cell images for each cell; measuring a plurality of different structural biosignatures for each cell from its 3D cell image to produce feature data; analyzing the feature data by first using cancer case status as ground truth to supervise development of a classifier to test the degree to which the features discriminate between cells from normal or cancer patients; using the analyzed feature data to develop classifiers including, a first classifier to discriminate normal squamous cells from normal and cancer patients, a second classifier to discriminate normal macrophages from normal and cancer patients, and a third classifier to discriminate normal bronchial columnar cells from normal and cancer patients.

22 Claims, 9 Drawing Sheets

Related U.S. Application Data

(60) Provisional application No. 62/637,328, filed on Mar. 1, 2018, provisional application No. 62/636,769, filed on Feb. 28, 2018.

(51) Int. Cl.
| | |
|---|---|
| *G01N 15/1434* | (2024.01) |
| *G01N 33/483* | (2006.01) |
| *G06F 18/214* | (2023.01) |
| *G06F 18/243* | (2023.01) |
| *G06T 7/00* | (2017.01) |
| *G06T 11/00* | (2006.01) |
| *G06V 10/40* | (2022.01) |
| *G06V 10/762* | (2022.01) |
| *G06V 10/774* | (2022.01) |

(52) U.S. Cl.
CPC .... *G06F 18/2148* (2023.01); *G06F 18/24317* (2023.01); *G06T 7/0012* (2013.01); *G06T 11/003* (2013.01); *G06V 10/40* (2022.01); *G06V 10/762* (2022.01); *G06V 10/7747* (2022.01); *G01N 2015/1445* (2013.01); *G06T 2207/10101* (2013.01); *G06T 2207/30024* (2013.01); *G06T 2207/30096* (2013.01); *G06V 2201/03* (2022.01)

(58) Field of Classification Search
CPC .......... G01N 2015/1445; G06T 7/0012; G06T 11/003; G06T 2207/10101; G06T 2207/30024; G06T 2207/30096; G06V 10/40; G06V 2201/03

See application file for complete search history.

(56) References Cited

U.S. PATENT DOCUMENTS

| | | | |
|---|---|---|---|
| 7,738,945 B2 | 6/2010 | Fauver et al. | |
| 7,835,561 B2 | 11/2010 | Meyer et al. | |
| 7,907,765 B2 | 3/2011 | Fauver et al. | |
| 8,155,420 B2 | 4/2012 | Meyer et al. | |
| 8,254,023 B2 | 8/2012 | Watson et al. | |
| 2002/0150285 A1 | 10/2002 | Nelson | |
| 2009/0214096 A1* | 8/2009 | Andrushkiw | G06T 7/0012 702/19 |
| 2013/0077085 A1 | 3/2013 | Zahniser et al. | |
| 2013/0190198 A1 | 7/2013 | Gough et al. | |
| 2013/0201317 A1 | 8/2013 | Ortyn et al. | |
| 2017/0003267 A1 | 1/2017 | Meyer et al. | |
| 2017/0140533 A1 | 5/2017 | Nelson et al. | |
| 2017/0243051 A1 | 8/2017 | Chukka et al. | |
| 2022/0180973 A1 | 6/2022 | Kang et al. | |

OTHER PUBLICATIONS

Breiman, "Random Forests," *Machine Learning* 45:5-32, 2001.
Deans, *The Radon Transform and Some of Its Applications*, Dover Publications, Inc., Mineloa, New York, USA, 1993, 308 pages.
Di Muzio et al., "Maximum intensity projection," Radiopaedia.org, retrieved from https://doi.org/10.53347/rID-14801, retrieved on Apr. 26, 2022, 4 pages.
Fauver et al., "Three-dimensional imaging of single isolated cell nuclei using optical projection tomography," *Optics Express* 13(11):4210-4223, 2005.
Jabalee et al., "Identification of Malignancy-Associated Changes in Histologically Normal Tumor-Adjacent Epithelium of Patients with HPV-Positive Oropharyngeal Cancer," *Analytical Cellular Pathology*: Article ID 1607814, 9 pages.
Maimon et al., *The Data Mining and Knowledge Discovery Handbook*, Springer Science + Business Media, Inc., New York, 2005, 1378 pages.
Meyer et al., "The Cell-CT 3-Dimensional Cell Imaging Technology Platform Enables the Detection of Lung Cancer Using the Noninvasive LuCED Sputum Test," *Cancer (Cancer Cytopathol)* 123:512-523, 2015.
Meyer et al., "Patent Disclosure: Morphometric Genotyping of Cells in Liquid Biopsy using the Cell-CT," VisionGate, Inc., US-60467, 22 pages.
Meyer et al., "Automated cell analysis in 2D and 3D: A comparative study," *Pattern Recognition* 42:141-146, 2009.
Miyagawa et al., "Morphometric analysis of liver macrophages in patients with colorectal liver metastasis," *Clinical & Experimental Metastasis* 19:119-125, 2002.
Neumann et al., "Premalignant and Malignant Cells in Sputum From Lung Cancer Patients," *Cancer (Cancer Cytopathol)* 117:473-481, 2009.
Schapire et al., *Boosting: Foundations and Algorithms*, The MIT Press, Cambridge Massachusetts, London, England, 2012, 548 pages.
Schreiber et al., "Performance Characteristics of Different Modalities for Diagnosis of Suspected Lung Cancer," *Chest* 123:115S-128S, 2003.
Wilbur et al., "Automated 3-Dimensional Morphologic Analysis of Sputum Specimens for Lung Cancer Detection: Performance Characteristics Support Use in Lung Cancer Screening," *Cancer (Cancer Cytopathol)* 123:548-556, 2015.

* cited by examiner

MORPHOMETRIC DETECTION OF MALIGNANCY ASSOCIATED CHANGE

TECHNICAL FIELD

The present invention relates to optical tomography on a cellular and sub-cellular scale. More particularly, the invention relates to a system and method for morphometric detection of malignancy associated change (MAC).

BACKGROUND

Lung cancer is the second most prevalent cancer in the United States and is the most lethal (4). Over 31 million patients in the United States (US) are at high risk for the development of lung cancer, primarily due to a smoking history, and approximately 160,000 US patients die of lung cancer each year (4). Many attempts have been made to develop screening procedures for lung cancer. Traditional cytologic methods on sputum or bronchial wash specimens have been shown to be relatively insensitive, with only about 40-60% of patients with cancer having positive results and the majority of those being from endobronchial squamous carcinomas (5, 6, 7). One bright spot related to the cytology examination is the relatively high positive predictive value of this procedure—generally above 98% —meaning that a positive test is a reliable indicator of disease (7).

Early detection remains by far the most reliable and potent strategy in curing cancer. Many approaches, however, are limited by poor sensitivity or specificity that increase health care costs and potentially risk patient health through unneeded, invasive procedures. The association between cell morphology and cancer has been established and well documented in the literature of cell cytology. On the other hand, the tumor field effect potentially introduces subtle changes into cells that are cytologically normal that reside in tumor microenvironment. This phenomenon has given rise to the malignancy associated change (MAC) hypothesis[1].

In pursuit of such an early lung cancer detection system, advances in 3D imaging of biological cells using optical tomography have been developed by Nelson as disclosed, for example, in U.S. Pat. No. 6,522,775, issued Feb. 18, 2003, and entitled "Apparatus and method for imaging small objects in a flow stream using optical tomography," the full disclosure of which is incorporated by reference. Further major developments in the field are taught in Fauver et al., U.S. Pat. No. 7,738,945, issued Jun. 15, 2010, entitled "Method and apparatus for pseudo projection formation for optical tomography," (Fauver'945) and Fauver et al., U.S. Pat. No. 7,907,765, issued Mar. 15, 2011, entitled "Focal plane tracking for optical microtomography," (Fauver 765) the full disclosures of Fauver'945 and Fauver 765 are also incorporated by reference. Building on the teachings therein an early lung cancer detection technology has been developed by VisionGate, Inc. of Phoenix, AZ to provide measurement advantages that have the potential to greatly improve the operating characteristics of conventional morphologic cytology analyses. New systems related to such an early lung cancer detection test are described herein.

Processing in an optical tomography system begins with specimen preparation. Typically, specimens taken from a patient are received from a hospital or clinic and processed to remove non-diagnostic elements, fixed and then stained. Stained specimens are then mixed with an optical gel, inserted into a microcapillary tube and images of objects, such as cells, in the specimen are produced using an optical tomography system. The resultant images comprise a set of extended depth of field images from differing perspectives called "pseudoprojection images." The set of pseudoprojection images can be reconstructed using backprojection and filtering techniques to yield a 3D reconstruction of a cell of interest. The ability to have isometric or roughly equal resolution in all three dimensions is an advantage in 3D tomographic cell imaging, especially for quantitative image analysis. The LuCED® test as implemented by Visiongate, Inc. of Phoenix Arizona is a promising new lung cancer detection method that produces high (92%) sensitivity and high (95%) specificity detection of lung cancer by imaging cells in true $3D^3$. In the LuCED® test, detection is managed through detection of abnormal cells in sputum. Imaging is provided by the Cell-CT™ platform, also manufactured by Visiongate, Inc., with sub micron, isometric spatial resolution in 3D.

The 3D reconstructions produced remain available for analysis in order to enable the quantification and the determination of the location of structures, molecules or molecular probes of interest. An object such as a biological cell may be labeled with at least one stain or tagged molecular probe, and the measured amount and location of this biomarker may yield important information about the disease state of the cell, including, but not limited to, various cancers such as lung, breast, prostate, cervical, stomach and pancreatic cancers.

In this document a method to detect the presence of cancer by analyzing subtle changes in cellular morphology imparted to non-cancer cells through the cancer field effect is disclosed. The method can be implemented in the Cell-CT™ platform. A process is disclosed that circumvents the need for the presence of cancer cells in the patient specimen. This is important especially for early cancer detection, as cancer cells are typically rare and thus difficult to detect in patient samples such as sputum, blood or biopsy material. This invention not only simplifies detection but also allows for more expedient processing of patient samples, as it does not require processing of cancer cells.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method for a system and method for morphometric detection of malignancy associated change (MAC) is disclosed including the acts of
  obtaining a sample;
  imaging cells to produce 3D cell images for each cell;
  measuring a plurality of different structural biosignatures for each cell from its 3D cell image to produce feature data;
  analyzing the feature data by first using cancer case status as ground truth to supervise development of a classifier to test the degree to which the features discriminate between cells from normal or cancer patients;
  using the analyzed feature data to develop classifiers including,
    A) a first classifier to discriminate normal squamous cells from normal and cancer patients,
    B) a second classifier to discriminate normal macrophages from normal and cancer patients, and C) a third classifier to discriminate normal bronchial columnar cells from normal and cancer patients.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
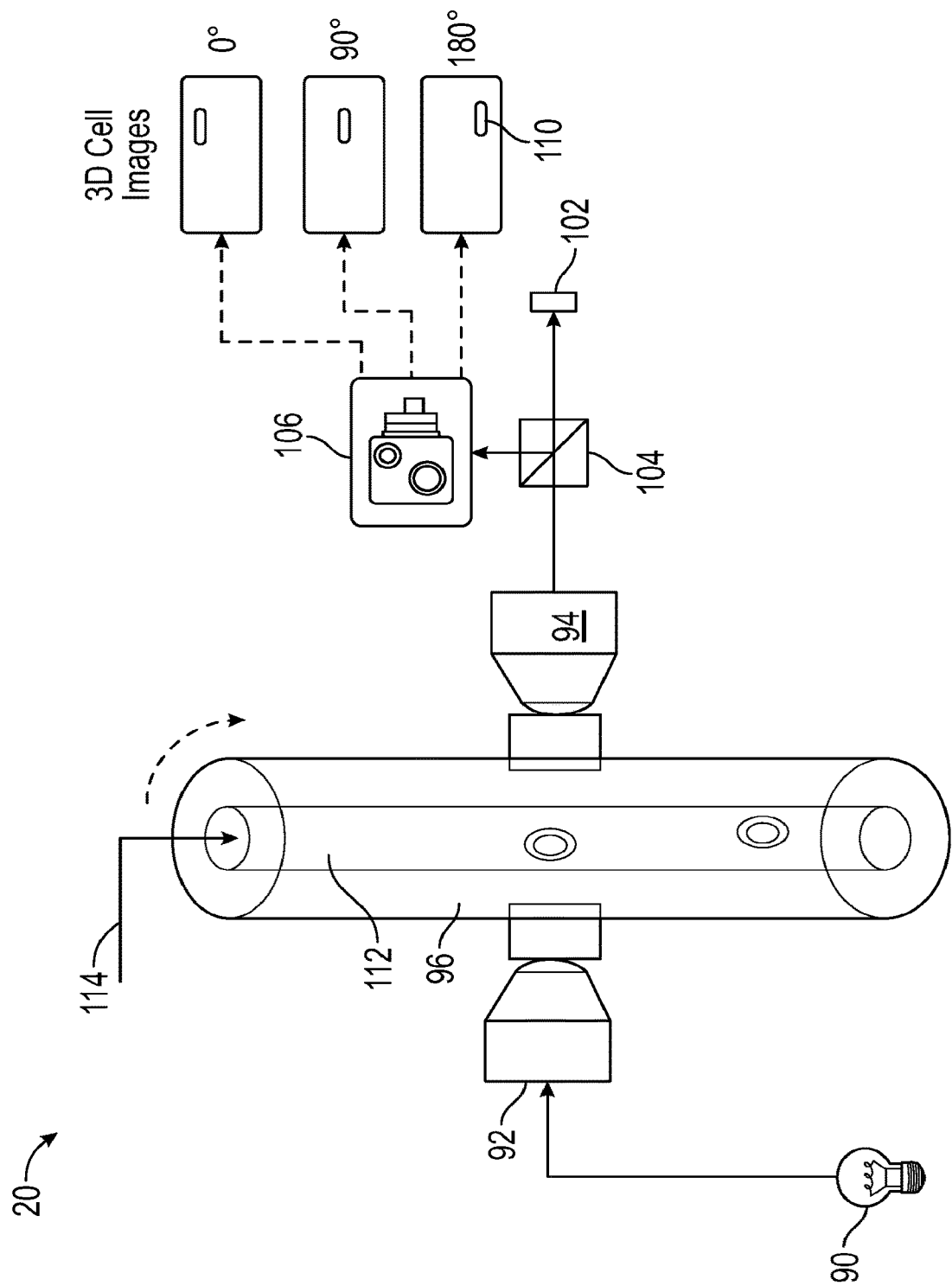
FIG. 1 schematically shows basic system components of a 3D optical tomography imaging system used in a lung cancer test system.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements and have been solely selected for ease of recognition in the drawings.

DETAILED DESCRIPTION OF THE PREFERRED EMBODIMENTS

The present invention provides an early lung cancer detection system using a method to detect the presence of cancer by analyzing subtle changes in cellular morphology imparted to non-cancer cells through the cancer field effect. A process is disclosed that circumvents the need for the presence of cancer cells in the patient specimen. This is important especially for early cancer detection, as cancer cells are typically rare and thus difficult to detect in patient samples such as sputum, blood or biopsy material. This invention not only simplifies detection but also allows for more expedient processing of patient samples, as it does not require processing of actual cancer cells in a sample.

It will be appreciated that methods and systems in accordance with other example embodiments can include additional procedures or features different than those shown in the figures. Example embodiments are described herein with respect to an optical tomography cell imaging system. However, it will be understood that these examples are for the purpose of illustrating the principles, and that the invention is not so limited.

Definitions

Generally, as used herein, the following terms have the following meanings:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise," "have," "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Capillary tube" has its generally accepted meaning and is intended to include transparent microcapillary tubes and equivalent items with an inside diameter generally of 500 microns or less.

"Cell-CT™ platform" refers to an optical tomography system manufactured by VisionGate, Inc. of Phoenix, AZ incorporating the teachings of the Nelson and Fauver patents referenced hereinabove. The Cell-CT is an automated, high-resolution optical 3D tomographic microscope and computing system for 3D imaging cells in flow. The Cell-CT™ platform computes 3D cell images with equal spatial resolution in all three dimensions (isotropic resolution) allowing measurements to be independent of orientation, as opposed to the conventional optical imaging methods that suffer from inferior resolution along the optical axis. Further, eliminating the focal plane ambiguity and view orientation dependencies typical of conventional microscopy provides information content to automatically recognize a broad spectrum of cell types, and unambiguously identify rare abnormal cells in a predominantly normal cell population.

"Depth of field" is the length along the optical axis within which the focal plane may be shifted before an unacceptable image blur for a specified feature is produced.

"Object" means an individual cell, item, thing or other entity.

"Pseudoprojection" includes a single image representing a sampled volume of extent larger than the native depth of field of the optics. The concept of a pseudoprojection is taught in Fauver'945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

Referring to FIG. 1, basic system components of a 3D optical tomography imaging system used in a lung cancer test system are shown. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high-speed camera produces a plurality of pseudo-projection images 110. A set of pseudo projection images for numerous axial tube rotation positions is produced for each object.

Although the test system is not limited to any one contrast method, in one example the lung cancer detection test specifically targets cell morphology based on the traditionally used hematoxylin stain. In the lung cancer detection test application, the optical tomography system computes 3D cell images with equal resolution in all dimensions (i.e., isotropic resolution) allowing measurements to be independent of orientation. Further, eliminating the focal plane ambiguity and view orientation dependencies typical of conventional microscopy provides information content to automatically recognize a broad spectrum of cell types, and unambiguously identify rare abnormal cells in a predominantly normal cell population. The optical tomography system output identifies about 0.5% of all cells as abnormal candidates to be verified using the CellGazer™ workstation (VisionGate, Phoenix, Ariz.), an imaging software tool that allows human review of images free of focal plane and orientation ambiguity.

The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, Optical Tomography System with High-Speed Scanner," which is also incorporated herein by reference. In operation stained nuclei of a biological cell 1 are suspended an optical media 112 and injected into a capillary tube 96 having, for example, a 62 μm inner diameter. The capillary system has been designed to be disposable, thus eliminating the possibility of cross-contamination between specimens. Pressure 114 applied to the fluid moves objects 1 into position for imaging, before 3D data is collected as the tube rotates. A mirror 102 is actuated to sweep the plane of focus through the object, and the image is integrated by the camera to create a pseudo-projection from each single perspective. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses. A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell may be rotated to allow capture of a set of 500 pseudo-projections is taken as the capillary rotates through 360 degrees.

Because the cells are suspended in a fluid medium, they are prone to a small amount of movement while pseudo-projection images 110 are collected. Cell images in the pseudo-projections, therefore, must be registered to a common center so that the cell features reinforce one another during the reconstruction. U.S. Pat. No. 7,835,561, entitled "Method for Image Processing and Reconstruction of Images for Optical Tomography," discloses error correction techniques for pseudo-projections. U.S. Pat. No. 7,835,561, is hereby incorporated by reference. The set of corrected pseudo-projections is processed using a filtered back-projection algorithm, similar to that in use in conventional X-ray CT, to compute the tomographic 3D cell reconstruction. Pseudo-projections images 110 taken at three angular positions: 0 g, 90 g and 180 g are shown. Illumination is provided by a light source 90 at 585 nm wavelength to optimize image contrast based on the hematoxylin absorption spectrum. In the reconstruction, 3D pixels or voxels are cubic, with a size of 70 nm in each dimension. Reconstruction volumes vary in size, as the image collection volume is cropped around the object. Typically, volumes are approximately 200-300 pixels on the side. One example of such a test system is the Cell-CT™ imaging platform made by Visiongate, Inc. Cell-CT™ imaging is performed on a small-volume liquid suspension of cells. Because the Cell-CT is adept at separating closely coincident objects, a narrowly focused core of single file cell flow (a requirement in standard flow cytometry) is unnecessary.

Sputum collection is typically done through spontaneous coughs in the patient's home or through induction in a clinic. Sputum is processed to remove contaminants and non-bronchial epithelial cells as, for example, by de-bulking the white cells and oral squamous cells. The enriched specimen is processed on the Cell-CT™ platform that images cells digitally in true 3D with isometric, sub-micron resolution as disclosed, for example in Nelson and Fauver referenced above. The bio signatures associated with cancer are measured on the 3D cell images and combined into a score that is used to identify those few cells that have cancer characteristics. These cells are then optionally displayed for manual cytologic review using a review station such as a CellGazer™ review station as developed by VisionGate, Inc., Phoenix, Ariz. The review station provides visual displays allowing a cytologist to view cell images in 2D and 3D to establish a definitive normal or abnormal status for specific cell candidates. Three-dimensional (3D) cell classification 22 may be carried out using techniques as disclosed herein below.

The cell imaging system 20 includes a process implemented through computer software executed, for example, by a personal computer interfacing with opto mechanical devices to correct for motion arising during image capture. Most cell images emerge from filtered back-projection in a well-reconstructed way. One example of a method for detecting poor quality reconstructions is taught by Meyer et al. in U.S. Pat. No. 8,155,420, issued Apr. 10, 2012 and entitled "System and Method for Detecting Poor Quality in 3D Reconstructions," the disclosure of which is incorporated herein by reference.

Earlier attempts at the development of a lung cancer-screening program were based on sputum cytology which showed an insufficient sensitivity to disease detection by human eye (about 60% on average) but with very good specificity (Schreiber and McCrory (2003) Chest 123 (1 Supplement): 115). This experience led some to conclude that sputum is not valuable for detection of lung cancer. A careful analysis involving sputum embedded in paraffin blocks (Bocking A, Biesterfeld S, Chatelain R, Gien-Gerlach G, Esser E., Diagnosis of bronchial carcinoma on sections of paraffin-embedded sputum. Sensitivity and specificity of an alternative to routine cytology. Acta Cytol. 1992; 36(1):37-47) showed that the specimen actually contains abnormal cells in 86% or more of cancer patients. Collection by morning coughs over three successive days yielded optimal results. A further analysis showed that abnormal cells are present in sputum stratified by all relevant clinical factors, including tumor histologic type, size, stage and location (Neumann T, Meyer M, Patten F, Johnson F, Erozan Y, Frable J, et al. Premalignant and Malignant Cells in Sputum from Lung Cancer Patients. Cancer Cytopathology, 2009; 117(6):473-481). Based on these specimen characteristics, the presently disclosed lung cancer detection test employs spontaneous cough sputum. Initial evaluations have shown satisfactory results using sputum fixation by either Cytoyt (Hologic, Marlborough, Mass.) or the well-known Saccomanno's method. The question of specimen adequacy is also important for sputum cytology. Attempts at increasing the volume of the sputum expectorate have met with varied success. Sputum induction increases production of phlegm to help achieve an overall adequate sample.

Figure 2:
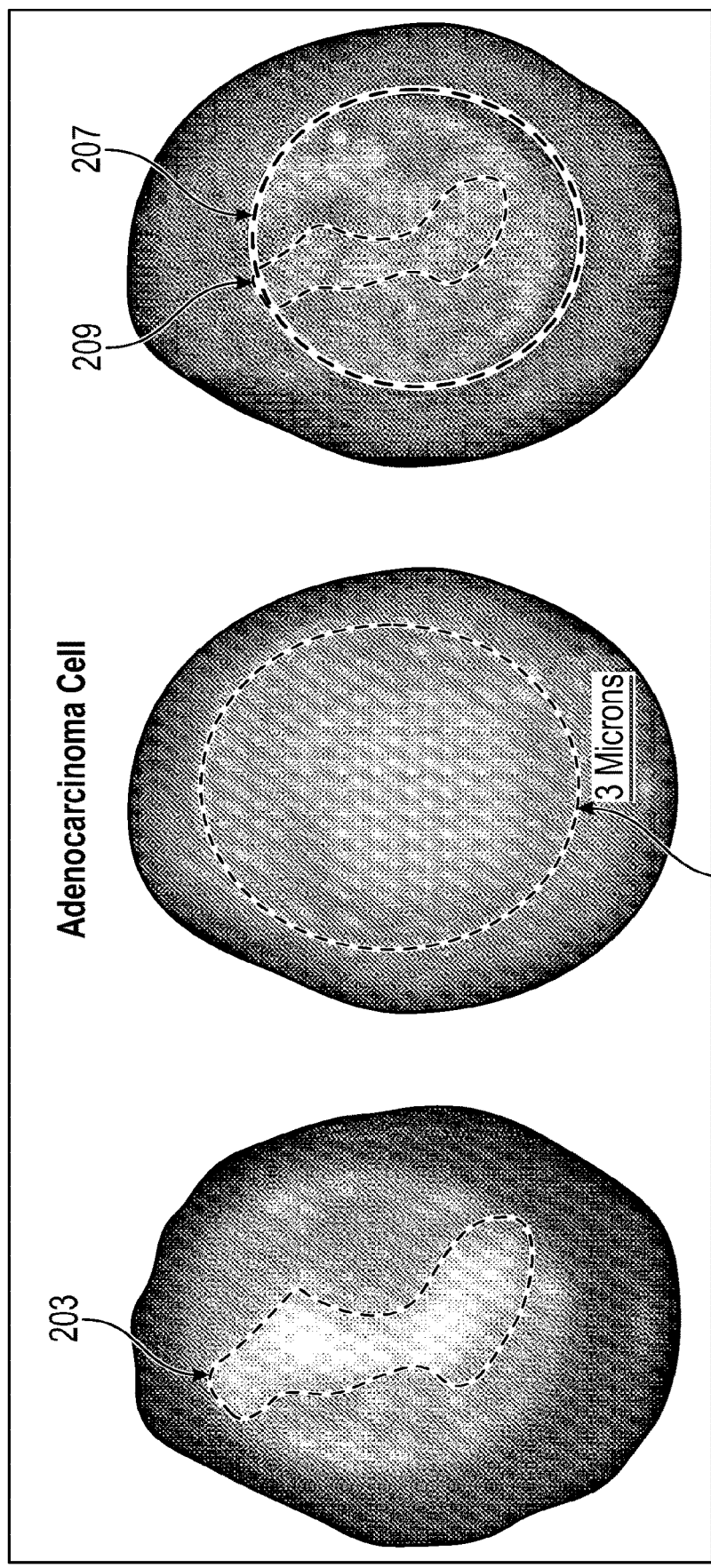
FIG. 2A-FIG. 2C show single perspective views of a 3D image of an adenocarcinoma cell.

Referring now to FIG. 2A-FIG. 2C single perspective views of a 3D image of an adenocarcinoma cell are shown. FIG. 2A shows the adenocarcinoma cell in maximum intensity projection. Since grey values in the 3D image are associated with various cell features a look-up table that maps cell structures to color and opacity values was established to produce the cell image at center (as shown in FIG. 2B) and right (as shown in FIG. 2C). In color reproductions of these images, the cytoplasm 203 is represented in translucent white as best shown in FIG. 2A, the nucleus 205 in opaque blue(center area shown in 2B), the loose chromatin and nucleoplasm in translucent green 209 and the condensed chromatin, and nucleoli are represented in opaque red 207 best shown in FIG. 2C.

Figure 3:
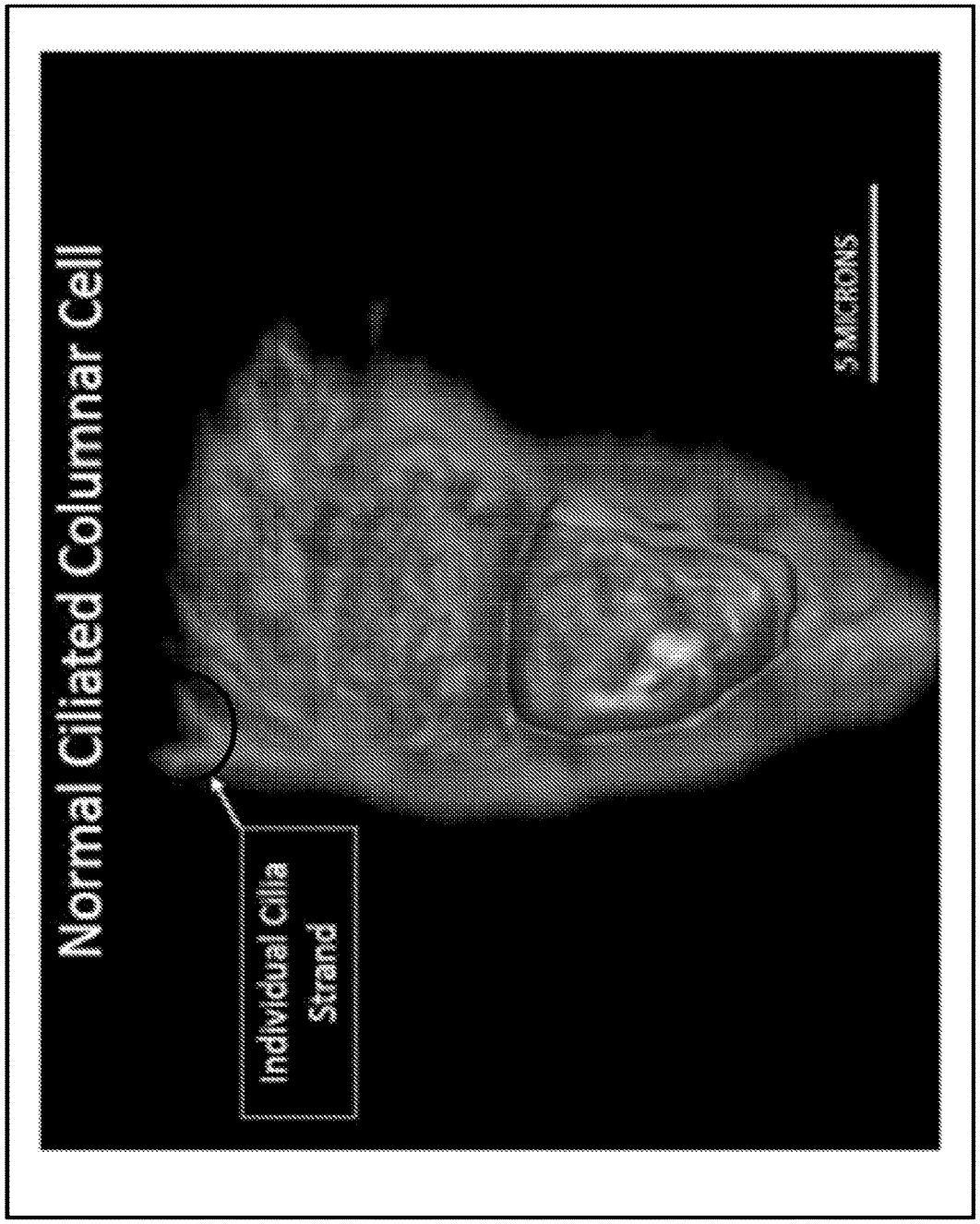
FIG. 3 shows cilia on lung columnar cell.

Referring now to FIG. 3, cilia on a lung columnar cell are shown. An imaged normal bronchial epithelial cell showing individual cilia strands measuring about 250 nm in diameter. This further demonstrates the resolution of the 3D cell imaging system.

Figure 4:
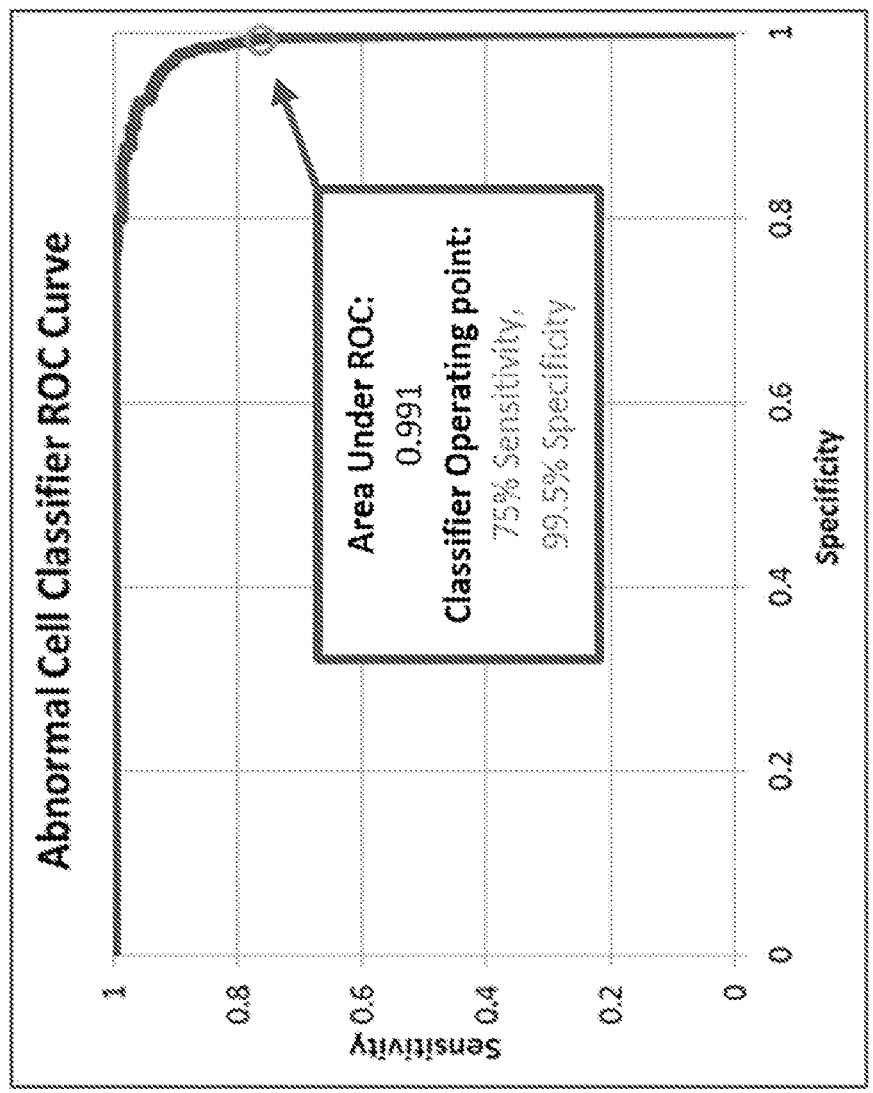
FIG. 4 graphically shows an abnormal cell classifier receiver operating (ROC) curve.

Referring now to FIG. 4, an abnormal cell classifier receiver operating (ROC) curve is graphically shown. The ROC plot sensitivity versus specificity for an abnormal cell classifier. In this example, the area under ROC is 0.991 with the classifier operating point showing 75% sensitivity and 99.5% specificity. This illustrates how the full potential of the Cell-CT technology arises from rapid automated analysis of 3D cell imagery, which can detect cell morphology features that are too subtle or too complex for human reviewers to discern. Furthermore, automated classification eliminates highly variable human review of specimens—a substantial limitation in clinical pathology. Moreover, classification based on 3D images sidesteps inherent limitations associated with classification based on standard 2D, fixed focal plane images, as the 2D slice may not carry the essential image information to comprehensively identify the cell disease state[6]. Infrastructure needed to define classifiers to detect abnormal cells is summarized in the points below:

Three-dimensional, verified, image segmentation to separate the whole cell from the background and the nucleus from the rest of the cell.

Morphological features defined to describe various aspects of the cell, cytoplasm, nucleus, and nucleoli. 704 features are computed that represent object shape, volume, distribution of chromatin, and other, more subtle, morphometric elements such as texture. Computation of these features has been verified to be independent of orientation of the cell.

The LuCED test referenced above encompasses the calculation of 704 features for each one of the normal and abnormal cells appearing in a sputum specimen. Features represent differing aspects of cellular morphology and include measures of cell and nuclear volume, ratio of nucleus to cytoplasm volume nuclear shape, cell shape, nuclear and cell centroids and their differentials. Another very important class of features describes the distribution of chromatin within the nuclear compartment. These features include enumeration of macro-nucleoli or nuclear wall invaginations whose presence correlates with the development of cancer. In general, the features aim to represent cell morphological signatures that have been found to be useful in discriminating normal from abnormal cells. Feature processing begins with segmentation which identifies the boundaries of the cell, the nucleus and the macronucleoli. Segmentation allows the feature computation to be focused only on those voxels (3D pixels) that are associated with the cell and its subcomponents as opposed to the background of voxels in which the cell is positioned. Classification aims to develop a set of weighted sums of a subset of the features that approximates the binary status (from a normal or cancer patient). The classifier was trained using methods to address other machine learning problems such as face recognition and voice recognition. These methods include Adaptively Boosted Logistic Regression[7] and Random Forest[7].

This effort has produced the ROC curve shown in FIG. 4 that illustrates the ability of LuCED to isolate and classify abnormal cells that are found in sputum.

Figure 5:
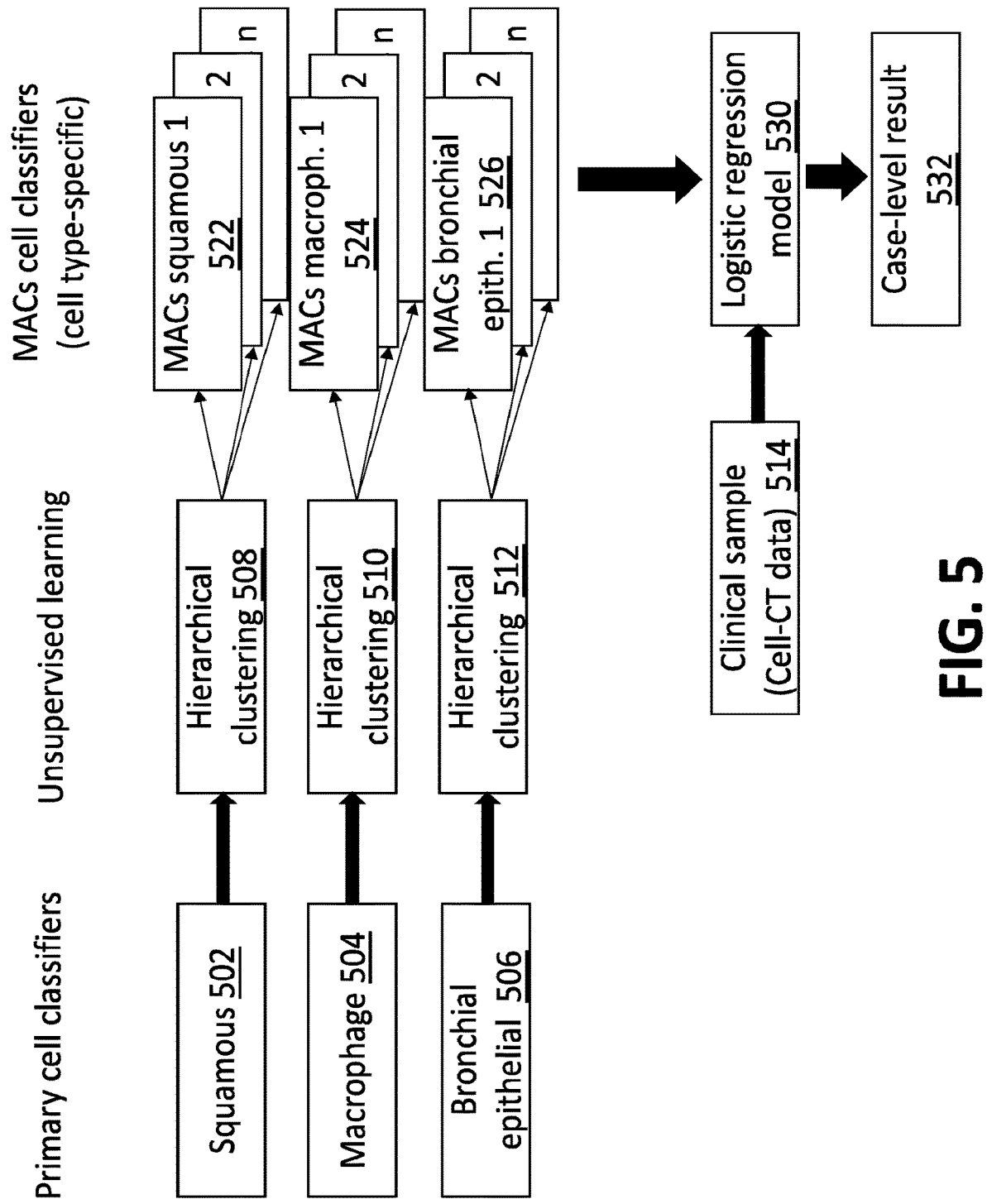
FIG. 5 shows the overall approach for developing cell type-specific MACs-related classifiers to distinguish between normal cells and cells carrying a MACs morphometric biosignature.

Referring now to FIG. 5, an overall approach for developing cell type-specific MACs-related classifiers to distinguish between normal cells and cells carrying a MACs morphometric biosignature is shown. The system includes a set of primary cell classifiers 502, 504, 506, a set of unsupervised learning classifiers 508, 510 and 512, and a set of MAC cell classifiers 522, 524, 526. The primary cell classifiers include a squamous cell classifier 502, a macrophage classifier 504, and a bronchial epithelial cell classifier 506. Each of the primary cell classifiers provide a classification output to one of three hierarchical clustering unsupervised learning algorithmic systems 508, 510 and 512 respectively. The first of the hierarchical clustering algorithmic systems 508 provides trained classification data to a plurality of first MAC cell classifiers 522, MAC squamous-1 through Max squamous cell n, where n is an integer number. The second of the hierarchical clustering algorithmic systems 510 provides trained classification data to a plurality of second MAC cell classifiers 524, MAC macrophage-1 through MAC macrophage cell n, where n is an integer number. The third of the hierarchical clustering algorithmic systems 512 provides trained classification data to a plurality of third MAC bronchial epithelial cell classifiers 526, MAC bronchial epithelial-1 through MAC bronchial epithelial cell n, where n is an integer number. Outputs from the three pluralities of MAC cell classifiers 522, 524 and 526 are generated and transmitted to a logistic regression model 530. Clinical samples of, for example, sputum from a human patient, are then input into the logistic regression model 530 which generates a case-level result 532 for the clinical sample 514.

Outputs from the three pluralities of MAC cell classifiers 522, 524 and 526 are generated and transmitted to a logistic regression model 530. Clinical samples of, for example, sputum from a human patient, are then input into the logistic regression model 530 which generates a case-level result 532 for the clinical sample.

Examples: Cell-CT Detection of Malignancy Associated Changes

A study conducted by the inventors here that focused on 3D morphological alterations in non-tumor cells obtained from sputum of normal and biopsy confirmed lung cancer patients indicates correlation between alterations in a panel of morphological features and the presence of cancer. Three major cell types derived from a total of 235 patients were analyzed: bronchial epithelial columnar, squamous intermediate and mature macrophages (dust cells). Cells were obtained from two types of patients: 1) biopsy confirmed cancer patients, 2) patients with no known cancer (normal patients). Cell diagnoses were confirmed by two independent cytotechnologists. Table 1 identifies the number cells processed in the differing categories:

TABLE 1

Numbers of Cells Used for MAC Classifier Training and Analysis

| Cell Type | Number of cells from cancer patients | Number of cells from normal patients |
| --- | --- | --- |
| Squamous Intermediate | 67,374 | 75,277 |
| Macrophages | 12,348 | 13,890 |
| Bronchial epithelial cells | 49,7494 | 59,578 |

The Cell-CT™ platform was used to image cells in 3D and to automatically measure at least 700 and up to 969 different structural features or more for each cell. Feature data was analyzed using an approach detailed in FIG. 5. First, cancer case status was used as ground truth to subdivide cells of the three types into those derived from normal and cancer samples Second, unsupervised clustering and ADABOOST7 methods were used for developing single-cell level classifiers to distinguish potential cancer-associated changes in squamous, columnar, and macrophage cells.

Clustering: approximately 20,000 randomly selected cells from known normal and cancer cases were used to perform hierarchical feature clustering using the Ward method. The clustering three was cut at 6 clusters and an ADABOOST[7] classifier was developed for each of the clusters using cells from the cluster as positives and cells of the same type, but derived from the normal samples as classifier negatives. The final result was a total of 18 separate classifiers (6 classifiers×3 cell types). The classifiers were applied to the entirety of the IASLC data with each classifier applied to its corresponding cell type. A threshold of 0.5 was applied to all 18 scores and the number of classifier positives was counted at the sample level. The number of classifier positives was normalized against the total number of cells of the corresponding type detected for each case. The ratios of the classifier positives to the total number of cells were used to develop a multiparameter logistic regression model.

The studies above used the case status (normal or cancer) as the ground truth only to subdivide the cells of the three different cell types into ones that are derived from normal and cancer samples and to assess sample-level logistic model performance. Model performance was characterized by the area under the ROC curve (aROC).

Figure 6A:
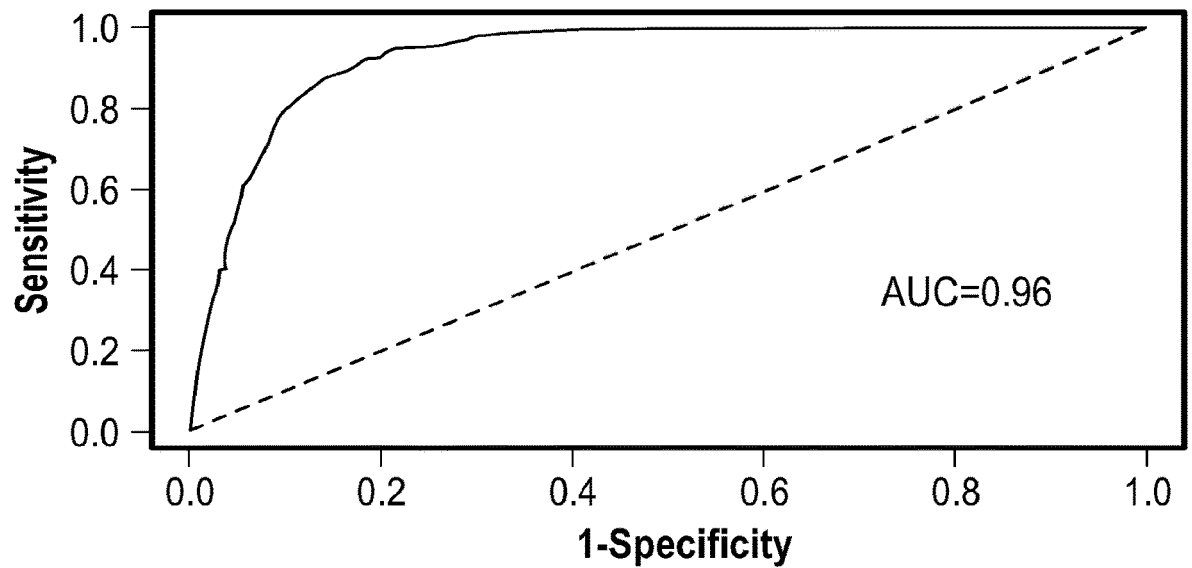
FIG. 6A and FIG. 6B graphically show example ROC curves of 2 selected single-cell level MACs classifiers trained to separate macrophages with a MACs biosignature from macrophages derived from normal sputum samples. Area under the curve (AUC) values are as indicated.
Figure 6B:
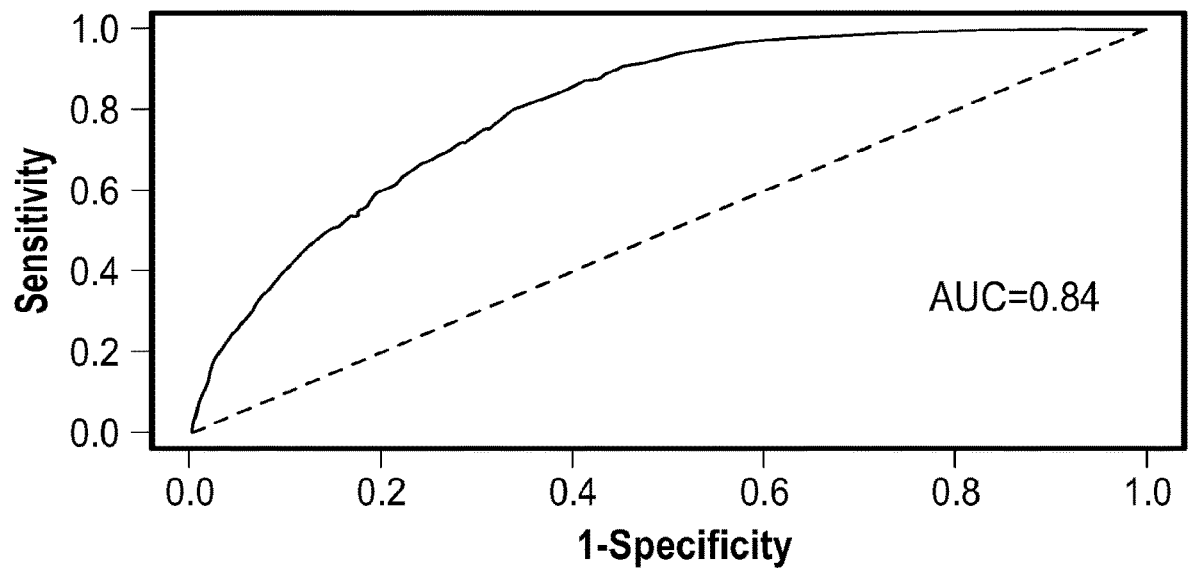
Figure 7:
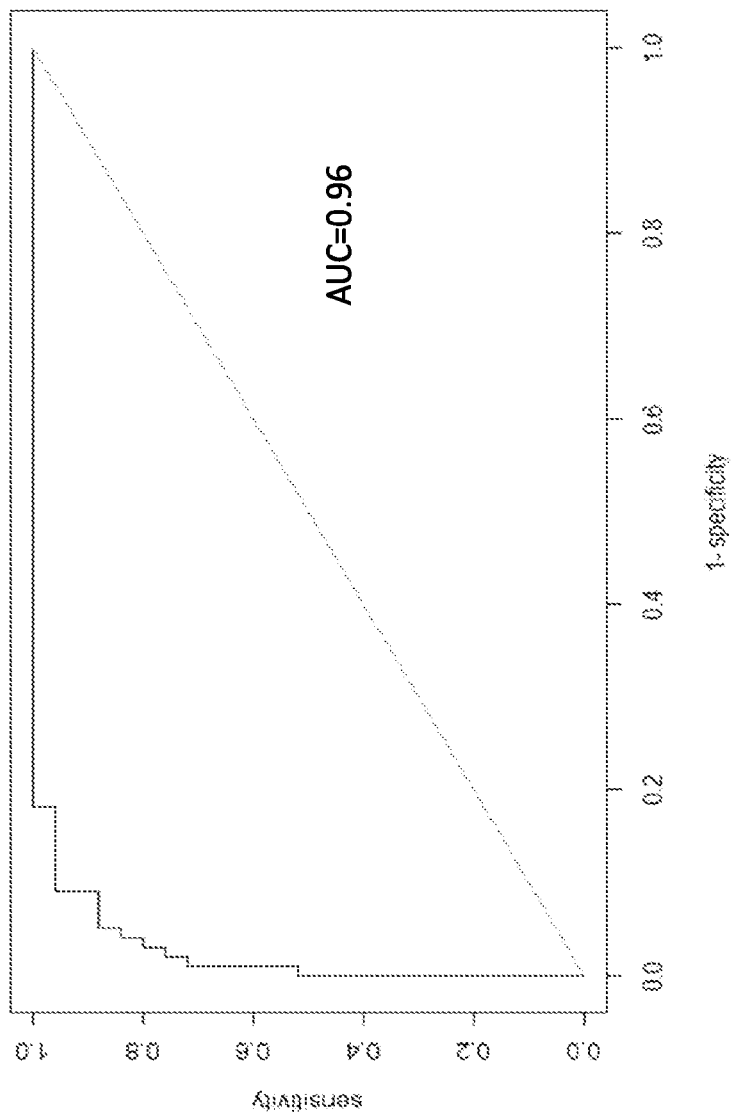
FIG. 7 graphically shows a ROC curve of a case-level classifier obtained using the logistic regression model and a validation dataset that was not used in the model derivation.
Figure 8:
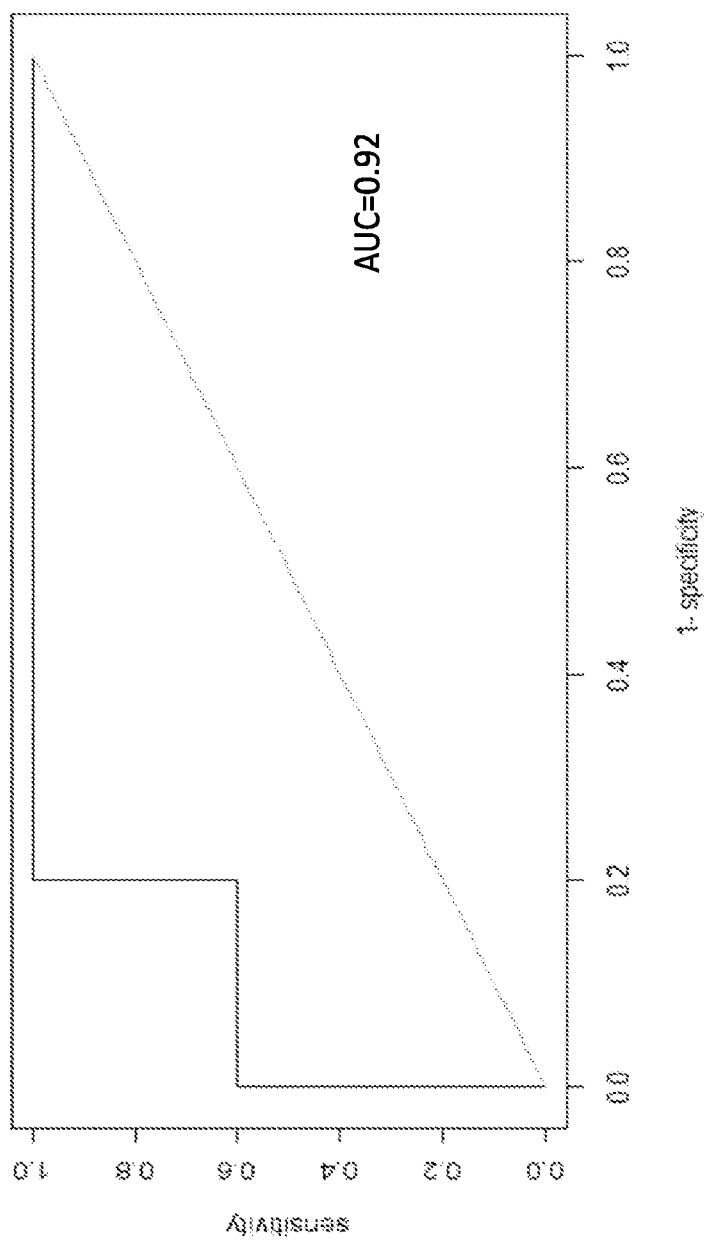
FIG. 8 graphically shows a ROC of the linear regression model when used on an independent dataset of limited size. The AUC value is 0.92

Referring now to FIG. 6A and FIG. 6B, example ROC curves of two separate single-cell level macrophage classifiers and their corresponding AUC values are shown. The sample-level model performance was evaluated using a validation dataset that was not used in model derivation (as shown in FIG. 7). The model resulted in an AUC value of 0.96. A separate validation using an independent dataset of limited size obtained with a different Cell-CT instrument is shown in FIG. 8 where the AUC value is 0.92. The multi-parameter logistic regression model showed that among the tree cell types only macrophages provide statistically significant contribution to the model to distinguish between normal and cancer sputum samples.

A total of 620 3D morphology features spanning a variety of cellular structural aspects contribute to 3 (out of 6) independent MACs macrophage classifiers with different information content. The 3 classifiers contribute significantly to the sample-level model for distinguishing normal from cancer sputum samples.

Figure 9:
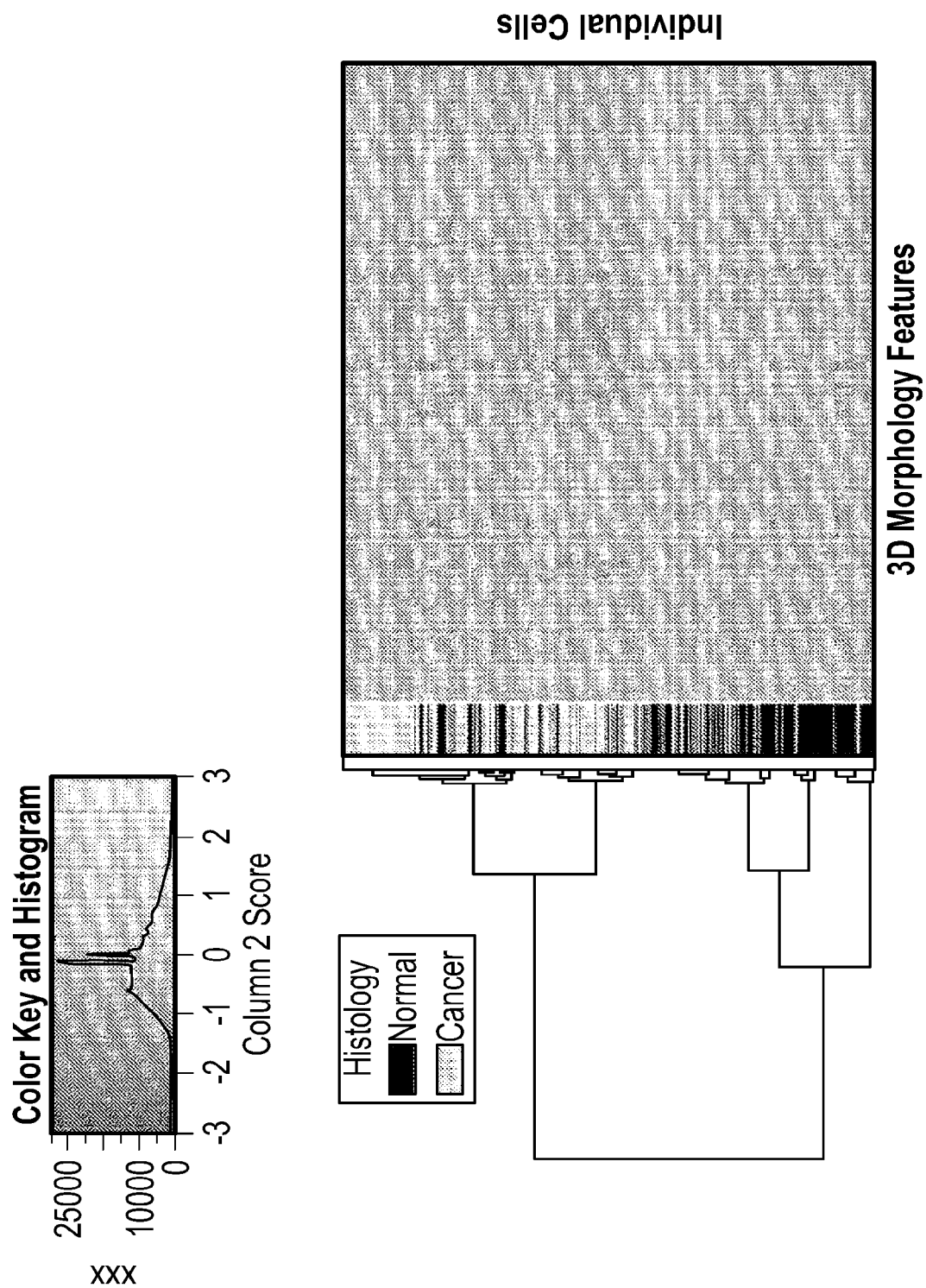
FIG. 9 is a heat graph showing a summary of results of clustering analysis using ~200 morphology features.

Referring now to FIG. 9, summary of results of clustering analysis using about 200 morphology features is shown. Features were further analyzed using hierarchical clustering using the same cells as for the macrophage classifier above. Cluster analysis is based on grouping objects based on their similarity. Objects that are more similar to one another than in other clusters (groups) are grouped together to reveal potential patterns on object distributions. In case of multi-parameter variables, as in CellCT data where 969 features are compared, the similarity measure can be based on several different factors. In one example, the connectivity based clustering also known as 'hierarchical clustering'[9] was used. The complete-linkage clustering method and Ward measure was used to calculate the dendrograms for clusters. The analysis showed that the most differentiating morphology features between macrophages from healthy subjects and patients with cancer are associated with the nuclear chromatin organization.

Results of this analysis are summarized in FIG. 9. Each column in the heatmap represents one feature, whereas rows represent individual cells. The shades of grey of the heatmap represent the difference between the individual value of a cell and the mean in units of standard deviation (Z-score) for each individual feature. The clustering dendrogram was produced using the Ward method with full connectivity.

The heatmap in FIG. 9 was produced using 211 morphology features that were most different between the normal and abnormal cases. A clear pattern of the feature values obtained from macrophages derived from normal subjects vs. cancer patients can be seen. The clustering analysis revealed 5 major clusters, with 4 clusters covering the majority of macrophages from normal samples and 1 major cluster encompassing the majority of macrophages from cancer patients. Together with the classifier characteristics presented above, this finding corroborates the MAC hypothesis. It further represents a proof-of-principle for the Cell-CT approach to detect cancer presence using non-cancer cells.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.
1. M. Guillaud A. Doudkine D. Garner C. MacAulay B. Palcic "Malignancy associated changes in cervical smears: Systematic changes in cytometric features with the grade of dysplasia" <em>Analytical Cellular Pathology</em> vol. 9 no. 3 pp. 191-24 Oct. 1995
2. Meyer M. et. al., The Cell-CT 3-Dimensional Imaging Technology Platform Enables the Detection of Lung Cancer Using the LuCED Sputum Test. Cancer Cytopathology, 123(9): 512-523, 2015
3. Wilbur D. et. al., Automated 3-Dimensional Morphologic Analysis of Sputum Specimens for Lung Cancer Detection: Performance Characteristics Support Use in Lung Cancer Screening. Cancer Cytopathology, 123(9): 548-556, 2015
4. Fauver M, Seibel E. Rahn J. Three-dimensional imaging of single isolated cell nuclei using optical projection tomography. Optics Express, 13:4210-4223, 2005.
5. Deans S. The Radon Transform and Some of Its Applications, New York: Dover Publishers: 2007
6. Rawski 2015
7. Schapire R, Freund Y. Boosting, Foundations and Algorithms, Cambridge: MIT Press, 2012
8. Breiman L. Random Forests. Machine Learning, 45:5-32, 2001
9. Rokach, Lior, and Oded Maimon. "Clustering methods." Data mining and knowledge discovery handbook. Springer US, 2005. 321-352.

What is claimed is:

1. A method for morphometric detection of malignancy associated change (MAC) after imaging cells in 3D, measuring a plurality of different structural biosignatures for each cell from its 3D cell image to produce feature data, and using the feature data and ground truth to supervise development of a target cell classifier to identify target cells, the method comprising:
   identifying clusters of target cells within a collection of target cells in normal cases and biopsy confirmed cancer cases;
   developing discriminant features between cell clusters to produce MACs cell classifiers; and
   executing a classifier to create a malignancy-associated change classifier case level result, wherein the classifier was trained using supervised machine learning based on the MACs cell classifiers and ground truth based on cancer/normal case status.

2. The method of claim 1, wherein the feature data comprises at least 200 morphology features.

3. The method of claim 1, wherein the target cells are macrophages identified through a supervised learning process based on features and cytology, rendered cell identification as macrophage or nonmacrophage.

4. The method of claim 1, wherein target cells are squamous cells identified through a supervised learning process based on features and cytology, rendered cell identification as squamous or nonsquamous.

5. The method of claim 1, wherein target cells are columnar cells identified through a supervised learning process based on features and cytology, rendered cell identification as columnar or noncolumnar.

6. The method of claim 1, wherein target cells are bronchial epithelial cells (BEC)s identified through a supervised learning process based on features and cytology, rendered cell identification as BEC or nonBEC.

7. The method of claim 1, wherein normal target cell classifiers are produced through adaptively boosted multivariate logistic regression.

8. The method of claim 1, wherein clusters are defined through unsupervised learning methods.

9. The method of claim 1, wherein MACs cell classifiers between clusters are based on adaptively boosted logistic regression.

10. The method of claim 1, wherein the malignancy-associated change case level result is produced through supervised learning using adaptively boosted logistic regression.

11. The method of claim 1, wherein the sample is a sputum specimen, blood specimen, or biopsy material specimen.

12. A system for morphometric detection of malignancy-associated change (MAC) after imaging cells in 3D, measuring a plurality of different structural biosignatures for each cell from its 3D cell image to produce feature data, and using the feature data and ground truth to supervise development of a target cell classifier to identify target cells, the system comprising:
   a memory that stores computer executable instructions; and
   a processor that executes the computer-executable instructions and cause the processor to:
      identify clusters of target cells within a collection of target cells in normal cases and biopsy confirmed cancer cases;
      develop discriminant features between cell clusters to produce MACs cell classifiers; and
      execute a classifier to create a malignancy-associated change classifier case level result, wherein the classifier was trained using supervised machine learning based on the MACs cell classifiers and ground truth based on cancer/normal case status.

13. The system of claim 12, wherein the feature data comprises at least 200 morphology features.

14. The system of claim 12, wherein target cells are macrophages identified through a supervised learning process based on features and cytology, rendered cell identification as macrophage or nonmacrophage.

15. The system of claim 12, wherein target cells are squamous cells identified through a supervised learning process based on features and cytology, rendered cell identification as squamous or nonsquamous.

16. The system of claim 12, wherein target cells is columnar cells identified through a supervised learning process based on features and cytology, rendered cell identification as columnar or noncolumnar.

17. The system of claim 12, wherein target cells are bronchial epithelial cells (BEC)s identified through a supervised learning process based on features and cytology, rendered cell identification as BEC or nonBEC.

18. The system of claim 12, wherein normal target cell classifiers are produced through adaptively boosted multivariate logistic regression.

19. The system of claim 12, wherein clusters are defined through unsupervised learning methods.

20. The system of claim 12, wherein MACs cell classifiers between clusters are based on adaptively boosted logistic regression.

21. The system of claim 12, wherein the malignancy-associated change case level result is produced through supervised learning using adaptively boosted logistic regression.

22. A system for morphometric detection of malignancy-associated change (MAC), the system comprising:
- a memory that stores computer executable instructions; and
- a processor that executes the computer-executable instructions and cause the processor to:
    - identify clusters of target cells within a collection of target cells in normal cases and biopsy confirmed cancer cases;
    - produce MACs cell classifiers using discriminate features from the identified clusters of target cells; and
    - execute a classifier to create a malignancy-associated change classifier case level result, wherein the classifier was trained using machine learning based on the MACs cell classifiers.

* * * * *